United States Patent

Satake

Patent Number: 5,389,340
Date of Patent: Feb. 14, 1995

[54] MODULE AND DEVICE FOR DETECTING NOX GAS

[75] Inventor: Kazuko Satake, Yokohama, Japan

[73] Assignee: Tokuyama Corporation, Japan

[21] Appl. No.: 811,240

[22] Filed: Dec. 20, 1991

Related U.S. Application Data

[63] Continuation-in-part of Ser. No. 458,380, Dec. 28, 1989, abandoned.

[51] Int. Cl.⁶ .............................................. G01N 27/00
[52] U.S. Cl. .................................. 422/98; 73/31.05; 73/31.06; 204/431; 422/90
[58] Field of Search ................... 422/90, 98; 73/31.05, 73/31.06; 204/153.14, 431; 501/134

[56] References Cited

U.S. PATENT DOCUMENTS

| | | | |
|---|---|---|---|
| 3,639,132 | 2/1972 | Egerton et al. | 501/134 |
| 3,951,603 | 4/1976 | Obayashi et al. | 73/31.05 X |
| 4,066,413 | 1/1978 | Segawa et al. | 422/98 |
| 4,169,369 | 10/1979 | Chang | 73/31.06 |
| 4,244,918 | 1/1981 | Yasuda et al. | 422/98 X |
| 4,358,950 | 11/1982 | Chang | 73/31.05 |
| 4,422,917 | 12/1983 | Hayfield | 204/291 X |
| 4,505,803 | 3/1985 | Mase et al. | 422/98 X |
| 4,547,314 | 10/1985 | Masuyama et al. | 501/136 X |
| 4,601,883 | 7/1986 | Sekido et al. | 422/98 X |
| 4,655,967 | 4/1987 | Morimoto et al. | 501/134 X |
| 4,706,493 | 11/1987 | Chang et al. | 422/98 X |
| 4,857,275 | 8/1989 | Furusaki et al. | 422/98 |
| 4,927,517 | 5/1990 | Mizutani et al. | 204/153.14 X |
| 4,953,387 | 9/1990 | Johnson et al. | 422/98 X |

FOREIGN PATENT DOCUMENTS

| | | |
|---|---|---|
| 2551743 | 3/1985 | France . |
| 56-54340 | 5/1981 | Japan . |
| 61-55749 | 7/1986 | Japan . |
| 61-147147 | 7/1986 | Japan . |
| 61-147149 | 7/1986 | Japan . |
| 1-150849 | 6/1989 | Japan .................... 422/98 |

*Primary Examiner*—James C. Housel
*Assistant Examiner*—Arlen Soderquist
*Attorney, Agent, or Firm*—Wenderoth, Lind & Ponack

[57] ABSTRACT

An element for detection of $NO_x$ gas in which at least one titanium-containing oxide which is selected from the group of (a) titanium oxide, (b) a solid solution wherein at least one element from the group of aluminum (Al), gallium (Ga), indium (In), scandium (Sc), magnesium (Mg), yttrium (Y), neodymium (Nd), tantalum (Ta), antimony (Sb) and arsenic (As) is contained in the solid-solution state in the titanium oxide, and (c) an oxide which contains titanium and other metal element(s) and has a perovskite structure, and has such an oxygen deficiency that its nonstoichiometric parameter ($\delta$) is in the range of 0.03 to 0.3. Thereby, $NO_x$ of an exhaust gas can be measured easily.

9 Claims, 1 Drawing Sheet

MODULE AND DEVICE FOR DETECTING NOX GAS

CROSS-REFERENCE TO RELATED APPLICATION

The present application is a continuation-in-part of the applicant's earlier U.S. patent application, Ser. No. 07/458,380, filed on Dec. 28, 1989, now abandoned.

The present invention relates to an element for detection of $NO_x$ gas consisting of NO and $NO_2$ in a mixed gas, a module for detection of $NO_x$, a device for detection of $NO_x$ and a process for detection of $NO_x$. More specifically, the invention relates to an element for detection of $NO_x$ gas which has a selectively high sensitivity to $NO_x$ in a mixed gas and an excellent sensitivity even in a high $NO_x$ concentration of several thousands ppm, and a series of techniques utilizing it.

Heretofore, nitrogen oxides NO and $NO_2$ in a mixed gas, especially exhaust gas, have been referred to as "$NO_x$", and measurement of the concentration of $NO_x$ has been carried out using a method such as a chemiluminescence method, infrared absorption method or electrolysis method. However, these methods have problems, for example, that they need large-sized devices and thus are costly and require maintenance.

For solution of these problems there have been developed elements for detection of $NO_x$ gas, as described below, using a certain semiconductor consisting of a metal oxide or an organic semiconductor such as a phthalocyanine complex, and devices for detection of $NO_x$ gas have been proposed which use the element for detection of $NO_x$ gas, and are small-sized and maintenance-free:

(a) U.S. Pat. No. 4,169,369 and SAE Technical Paper Series 800537

This U.S. patent discloses a method of detection or measurement of $NO_x$ gas in a mixed gas using a thin film comprising polycrystalline tin oxide having an oxygen to tin atomic ratio between 1.5 and 1.95, (b) Japanese Utility Model Publication No. 32360/1986

This Japanese Utility Model Publication discloses a semiconductor device for detection of nitrogen oxides which uses a $(NO+NO_2)$ gas sensor consisting of a $V_2O_5+Sm_2O_5+Ag$ semiconductor thin film layer and a $NO_2$ gas sensor consisting of a $V_2O_5+Ag$ semiconductor thin film layer.

(c) Sensor and Actuators, 16, (1989), 379–392

A paper titled "Kinetics factors in the response of organometallic semiconductor gas sensor" is carried in this literature, and results obtained when various phthalocyanine complexes are used as $NO_2$ sensors are reported therein.

On the other hand, it is disclosed in SAE Technical Paper Series 750224 published by Society of Automotive Engineers Inc. to use titania ($TiO_2$) as an air to fuel ratio sensor for automobile exhaust.

This literature discloses utilization of titania ($TiO_2$) as a sensor to detect oxygen partial pressure in an exhaust gas, and therein a titania ceramic is maintained at a temperature of 700° to 1,000° C. However, this literature is utterly silent about titania having oxygen deficiency and its utilization for detection of $NO_x$ gas.

The above $NO_x$ gas-detecting device using the $NO_x$ gas-detecting element or sensor is a device wherein a couple of electrodes are connected to the $NO_x$ gas-detecting element and wherewith change of electric resistance taking place when the $NO_x$ gas-detecting element absorbs $NO_x$ is measured to measure $NO_x$ amount. The device has drawn attention as a small-sized and maintenance-free $NO_x$ gas-detecting device.

However, the above usual $NO_x$ gas-detecting devices have the following problems due to characteristics of the $NO_x$ gas-detecting element:

(1) Due to their low sensitivity to NO, it is hard to accurately determine the $NO_x$ concentration of a gas wherein $NO_x$ occupies 90% or more of the contained $NO_x$ such as an exhaust gas from an internal combustion engine or the like.

(2) As the upper limit of quantitatively determinable $NO_x$ gas concentration is several hundreds ppm and thus low, they cannot be used for detection of a gas whose $NO_x$ concentration reaches even several thousands ppm such as an exhaust gas from an internal combustion engine or the like.

(3) As they have relatively high sensitivity also to other gases such as $O_2$, CO and hydrocarbon (HC) than $NO_x$ gas, it is hard to accurately determine $NO_x$ concentration of a gas containing both $NO_x$ gas and these gases.

(4) Concerning an organic semiconductor, it cannot be set inside the flue of an internal combustion engine or the like for lack of thermal stability.

Thus, the first object of the present invention is to provide an $NO_x$ gas-detecting element which exhibits high sensitivities to both NO gas and $NO_2$ gas in a mixed gas, namely a high sensitivity to the whole $NO_x$ gas.

The second object of the invention is to provide an $NO_x$ gas-detecting element which has a selectively high sensitivity to $NO_x$ gas whether the concentration of $NO_x$ gas contained is low or high.

Another object of the invention is to provide an $NO_x$ gas-detecting element having a selectively high sensitivity to $NO_x$ gas even when gases other than $NO_x$ gas such as $O_2$, CO and hydrocarbons are contained in a mixed gas.

Still another object of the invention is to provide an $NO_x$ gas-detecting element suitable for measurement of the concentration of $NO_x$ gas contained in an exhaust gas from an internal combustion engine.

Still another object of the invention is to provide an $NO_x$ gas-detecting module and an $NO_x$ gas-detecting device wherein the above $NO_x$ gas-detecting elements are used, respectively.

Still another object of the invention is to provide a process for measurement of $NO_x$ gas concentration in a mixed gas using the above $NO_x$ gas-detecting element.

Still other objects of the invention will be apparent from the following descriptions.

According to research by the present inventors it has been clarified that the above objects and benefits of the present invention can be accomplished by an element for detection of $NO_x$ gas substantially consisting of at least one titanium-containing oxide which is selected from the group consisting of (a) titanium oxide, (b) a solid solution wherein at least one element selected from the group consisting of aluminum (Al), gallium (Ga), indium (In), scandium (Sc), magnesium (Mg), yttrium (Y), neodymium (Nd), tantalum (Ta), antimony (Sb) and arsenic (As) is contained in the solid-solution state in the titanium oxide, and (c) an oxide which contains titanium and other metal element(s) and has a perovskite structure,
and has such an oxygen deficiency that its nonstoichiometric parameter ($\delta$) is 0.03 to 0.3.

Further, there are provided as a result of research by the present inventors a module for detection of $NO_x$ gas which is composed of an electric insulating support; the above $NO_x$ gas-detecting element which is integrated thereinto and exposed on the surface; and a couple of electrodes connected to the detecting element at intervals of distance, as well as a device for detection of $NO_x$ gas which is composed of the above $NO_x$ gas-detecting module; a power source; and a measurement equipment for measurement of the electric voltage or electric current or electric resistance in the $NO_x$ gas-detecting module and wherein the $NO_x$ gas-detecting module, the electric power source and the measurement equipment are electrically connected.

Further, there is provided as a result of research of the present inventors a process for measurement of the concentration of $NO_x$ gas in a mixed gas using the above $NO_x$ gas-detecting device, as later described.

The present invention is detailedly and specifically described below.

The $NO_x$ gas-detecting element of the present invention substantially consists, as above-mentioned, of at least one titanium-containing oxide which is selected from the group consisting of (a) titanium oxide, (b) the solid solution and (c) the oxide and has such an oxygen deficiency that its nonstoichiometric parameter ($\delta$) is in the range of 0.03 to 0.3.

The term "nonstoichiometric parameter ($\delta$)" means a rate in which the oxygen content is short compared to the stoichiometrically represented chemical formula, and can specifically be represented by the following chemical formula:

| Stoichiometric titanium-containing-oxide | Titanium-containing oxide of the invention |
|---|---|
| (a) $TiO_2$ | (a) $TiO_{2-\delta}$ |
| (b) $A_zTi_{1-z}O_2$ | (b) $A_zTi_{1-z}O_{2-\delta}$ |
| (c) $BTiO_3$ | (c) $BTiO_{3-\delta}$ | wherein A, B and z have later-described definitions, respectively.

Thus, it can be said that the titanium-containing oxide in the invention is a titanium-containing compound in such a state that its oxygen is deleted from a stoichiometric titanium-containing compound such as the above (a), (b) or (c) in the proportion of ($\delta$).

The value of the nonstoichiometric parameter ($\delta$) in the invention means a value calculated from the amount of each element measured using an ESCA (X-ray photoelectron spectral apparatus). That is, the nonstoichiometric parameter ($\delta$) of the $NO_x$ gas-detecting element is a value calculated from the amount of each element of the $NO_x$ gas-detecting element measured using an ESCA.

The titanium-containing oxide composing the $NO_x$ gas-detecting element of the invention has such an oxygen deficiency that the nonstoichiometric parameter ($\delta$) is in the range of 0.03 to 0.3, preferably 0.04 to 0.2, as above-described. Titanium-containing oxides having a nonstoichiometric parameter ($\delta$) smaller than the above range have a higher sensitivity to oxygen ($O_2$) and a much lower sensitivity to $NO_x$. On the other hand, when the above ($\delta$) goes beyond the above range, sensitivity to all gases is lowered to make utilization thereof as a detecting element impossible.

Thus, typical examples of the titanium-containing oxides composing the $NO_x$ gas-detecting elements of the invention are specifically indicated below:
(a-1) $TiO_{2-\delta}$,
(b-1) $A_zTi_{1-z}O_{2-\delta}$ or
(c-1) $BTiO_{3-\delta}$.

Each ($\delta$) in the above (a-1), (b-1) and (c-1) represents a nonstoichiometric parameter. These oxides are more detailedly described below.

$TiO_{2-\delta}$ of (a-1) is a titanium oxide having an oxygen deficiency to titanium dioxide.

$A_zTi_{1-z}O_{2-\delta}$ of (b-1) is a composite oxide containing the element A in the solid-solution state in titanium oxide, and the element A is Al, Ga, In, Sc, Mg, Y, Nd, Ta, Sb or As, or a mixture of two or more of them. The z in (b-1) represents the rate in which the element A is contained in the solid-solution state and is in the range satisfying $0 < z < 0.1$ when the element A is Al, Ga, In, Sc, Mg or Y and in the range satisfying $0 < z < 0.05$ when the element A is Nd, Ta, Sb or As. Specific examples of composite oxides of (b-1) include the following compounds:

$Al_zTi_{1-z}O_{2-\delta}$, $Ga_zTi_{1-z}O_{2-\delta}$,
$In_zTi_{1-z}O_{2-\delta}$, $Sc_zTi_{1-z}O_{2-\delta}$,
$Mg_zTi_{1-z}O_{2-\delta}$, $Y_zTi_{1-z}O_{2-\delta}$,
$Nd_zTi_{1-z}O_{2-\delta}$, $Ta_zTi_{1-z}O_{2-\delta}$,
$Sb_zTi_{1-z}O_{2-\delta}$, $As_zTi_{1-z}O_{2-\delta}$,
$Al_{z1}Nb_{z2}Ti_{(1-z1-z2)}O_{2-\delta}$,
$Ta_{z1}Sb_{z2}Ti_{(1-z1-z2)}O_{2-\delta}$,
$Ga_{z1}As_{z2}Ti_{(1-z1-z2)}O_{2-\delta}$,
$Y_{z1}Nb_{z2}Ti_{(1-z1-z2)}O_{2-\delta}$, wherein z is as defined above, and z1 and z2 represent positive numbers provided that they satisfy $z1+z2=z$.

Preferred ones among composite oxides of (b-1) are composite oxides wherein the above element A is Al, Ga, In, Sc, Y or Mg.

Further, the oxide of (c) in the invention which contains titanium and other metal element(s) and has a perovskite structure is represented by $BTiO_{3-\delta}$ as shown in the above formula (c-1). In the above formula, B is lead (Pb), calcium (Ca), strontium (Sr), cadmium (Cd), lanthanum (La) or barium (Ba) or a mixture of two or more of these metals.

Specific examples of the above oxides having a perovskite structure include, for example, $PbTiO_{3-\delta}$, $CaTiO_{3-\delta}$, $SrTiO_{3-\delta}$, $CdTiO_{3-\delta}$, $LaTiO_{3-\delta}$, $BaTiO_{3-\delta}$, $Sr_yBa_{1-y}TiO_{3-\delta}$, $Ba_yLa_{1-y}TiO_{3-\delta}$ and $Ca_ySr_{1-y}TiO_{3-\delta}$ wherein y is a positive number satisfying $0 < y < 1$.

Among the above oxides of a perovskite structure are preferred oxides wherein B in the above formula (c-1) is Ba, (Ba+La), Cd, or Sr.

It is needed that the $NO_x$ gas-detecting element of the invention is the aforementioned titanium-containing oxide, but not particularly limited about its shape. The shape may appropriately be determined in accordance with the structure of the $NO_x$ gas-detecting module or $NO_x$ gas-detecting device. Usually, the $NO_x$ gas-detecting element may, for example, have a chip-like or thin film-like structure. Such a chip-like element can specifically be, for example, a circular, rectangular or elliptic flake, and it is advantageous that the thickness of these flakes is 0.05 to 5 mm, preferably 0.1 to 3 mm and the area of one side of the flakes is in the range of 0.1 to 150 $mm^2$, preferably 0.3 to 100 $mm^2$. On the other hand, such a thin film-like element can be one which has a thickness in the range of $1 \times 10^{-5}$ to 0.3 mm, preferably $1 \times 10^{-4}$ to 0.2 mm and a film area of one side in the range of 0.001 to 100 mm$^2$, preferably 0.003 to 100 mm$^2$.

The preparation method of the titanium-containing oxide as the NO$_x$ gas-detecting element in the invention is not particularly limited, and may typically be a sintering method, sputtering method, vacuum evaporation method, thermal decomposition method or the like. Among these preparation methods the sintering method is suitable for molding of chip-like and thin film-like NO$_x$ gas-detecting elements, whereas the sputtering vacuum evaporation and thermal decomposition methods are suitable for obtaining film-like elements. These methods are described below:

(I) Sintering Method

Usually preferred as this sintering method is a method wherein powder of a titanium-containing oxide having the above-mentioned composition is packed into a cavity having a predetermined shape, and heated after, or simultaneously with, compression molding. Proper pressure in the compression molding is 200 kg/cm$^2$ to 1 t/cm$^2$, (t=metric ton), generally 300 to 700 kg/cm$^2$. In this method sintering temperature and sintering atmosphere have a particular important influence on determination of the nonstoichiometric parameter ($\delta$). In a nonreducing atmosphere (N$_2$, Ar or the like) the sintering temperature (T) may be a temperature in the range of 900° C.$<$T$<$the melting point of the titanium-containing oxide. The sintering temperature for case of using an atmosphere of a reducing gas such as CO or H$_2$ changes depending on the kind and concentration of the gas. However, it is desirable that the sintering temperature is 700° C.$<$T$<$1,000° C. in N$_2$ containing 5% CO and 600° C.$<$T$<$900° C. in N$_2$ containing 5% H$_2$. Further, it is of course possible to use a combination of the above sintering conditions, for example, a method wherein the titanium-containing oxide is first sintered in a nonreducing atmosphere and then treated in a reducing atmosphere.

There may be used as another sintering method a method wherein powder of the titanium-containing oxide is mixed with a dispersion medium to make paste, screen printing is made onto an insulating substrate using the paste to form a film, and the film is sintered at the above temperature and condition of sintering.

In the above sintering method, it is also possible to use as the starting material another titanium-containing compound such as a hydroxide or alkoxide of titanium in place of the titanium-containing oxide and oxidize and sinter the compound at the same time.

(II) Sputtering Method

There may, for example, be used as the sputtering method a method wherein sputtering is made onto an insulating substrate in the presence of oxygen using metal titanium or the like as a target material to form a thin film and the thin film is burned in the air at 500° to 800° C. to obtain a thin film of TiO$_2$.

(III) Vacuum Evaporation Method

There may, for example, be used as the vacuum evaporation method a method wherein metal titanium is evaporated under an oxygen pressure of 0.5 to 3 Torr and this vapor is deposited on an insulating substrate such as alumina to form a TiO$_2$ thin film.

(IV) Thermal Decomposition Method

There may be used as the thermal decomposition method a method wherein a mixed solution of an organo-metal compound such as an alkoxide of metal composing the desired titanium-containing oxide is applied onto a substrate such as alumina and thermally decomposed either in a nonreducing atmosphere, e.g. in the air or in a reducing atmosphere at 500° C. to a temperature equal to, or less than, their melting point to form a TiO$_2$ thin film.

Although the sputtering, vacuum evaporation and thermal decomposition methods were described about a process of preparation of a thin film of TiO$_2$, films of other titanium-containing oxides can be prepared in the same manner as above.

The above-described titanium-containing oxides of the invention have a fully satisfactory sensitivity to NO$_x$ gas in a mixed gas.

However, it has been found as a result of research by the present inventors that the concentration of NO$_x$ gas in a mixed gas containing besides NO$_x$ gas the aforementioned other gases in a low concentration to a high concentration can be measured in higher sensitivity and more accurately by making an oxidation catalyst exist at least on the surface of the element substantially consisting of the above titanium-containing oxide.

There is no particular limitation about the oxidation catalyst which is made to exist at least on the surface of the element of the invention so long as it displays performances of oxidation catalyst at a temperature at which the NO$_x$ gas-detecting element is used. Typical examples of such oxidation catalysts include noble metal type oxidation catalysts such as Pt, Rh and Pd, metal type oxidation catalysts such as Ni and Fe, metal oxide type oxidation catalysts such as LaCO$_3$, LaNiO$_3$ and LaSr$_{0.3}$Co$_{0.7}$O$_3$, etc. Particularly preferred among them are noble metal type oxidation catalysts such as Pt, Rh and Pd. It is quite enough that the above oxidation catalyst exists at least on the surface of the element consisting of the afore-mentioned titanium-containing oxide as a layer containing the oxidation catalyst. That is, there can be mentioned as the embodiments to make the layer containing the oxidation catalyst exist at least on the surface of the element comprising the titanium-containing oxide ① an embodiment wherein the oxidation catalyst is made to exist in a state dispersed throughout the element, ② an embodiment wherein the oxidation catalyst is made to exist in a state partially dispersed in the outer layer of the element, ③ an embodiment wherein an oxidation catalyst-containing layer is formed on the surface of the element; etc. Particularly preferred among them are the embodiments of ① and ②. In the embodiment of ③ the oxidation catalyst-containing layer may be formed by carrier particles carrying the oxidation catalyst or in some case by the oxidation catalyst alone.

The embodiments of ① and ② are suitable for the above noble metal type oxidation catalysts and metal type oxidation catalysts. The concentration of the noble metal type oxidation catalyst in the matrix of the titanium-containing oxide containing the oxidation catalyst is generally 10 to 1,000 ppm, preferably 100 to 600 ppm, whereas that of the metal type oxidation catalyst therein is generally 0.1 to 1 wt %, preferably 0.5 to 1 wt %. On the other hand, the embodiment of ③ is applicable to all type of the oxidation catalysts. Particularly for the noble metal type oxidation catalysts and metal type oxidation catalysts is suitable the method of forming a layer by carrying them on the surface of carrier particles, and the suitable concentration of the oxidation catalyst on the surface of the carrier particles in this case accords with the concentration range thereof in the above oxidation catalyst-containing matrix. Further, it is preferred that the metal oxide type metal catalyst forms a layer by the catalyst alone. In the embodiments of ② and ③ it is generally preferred that the thickness of the oxidation catalyst-containing layer is one micrometer or more.

There is no particular limitation in the invention about the method for formation of an oxidation catalyst-containing layer in or on the element consisting of the titanium-containing oxide. For example, for the embodiment of the above ① is suitable a method wherein in preparation of a titanium-containing oxide by the sintering method, thermal decomposition method or the like the oxidation catalyst or a compound capable of forming the oxidation catalyst by heating during sintering or thermal decomposition is compounded in the raw materials. Suitable for the embodiment of ② is a method wherein the titanium-containing oxide is impregnated with a solution of a compound capable of forming the oxidation catalyst by heating and then heated. Examples of compounds capable of forming oxidation catalysts include soluble salts of the above-described noble metals or metals such as chlorides, nitrates or organic acid salts. Further, for the embodiment of ③ is mentioned a method wherein the oxidation catalyst is attached onto the surface of the element consisting of the titanium-containing oxide by a method such as a sputtering, vaccum evaporation, sintering of thermal decomposition method; or a method wherein the oxidation catalyst is carried on carrier particles of $TiO_2$, $Al_2O_3$, $MgO \cdot Al_2O_3$, $SiO_2$ or the like and then the carrier particles are attached onto the surface of the element consisting of the titanium-containing oxide by a means such as sintering.

Although the $NO_x$ gas-detecting element of the invention substantially consists, as hereinbefore described, of the titanium-containing oxide having an oxygen deficiency optionally together with the oxidation catalyst, there is no hindrance about that a small amount of another oxide is contained therein within such a range that the nonstoichiometric parameter ($\delta$) of the $NO_x$ gas-detecting element of the invention is not much influenced. For example, the $NO_x$ gas-detecting element of the invention may contain in a small rate a titanium-containing oxide having such an oxygen deficiency that the nonstoichiometric parameter ($\delta$) is out of the range defined in the invention or a carrier to carry the oxidation catalyst such as $TiO_2$, $Al_2O_3$, $MgO$ $Al_2O_3$ or $SiO_2$. The amount of the oxide to be incorporated in the titanium-containing oxide depends on its kind, etc., but is on the order of 10 wt.% at most, preferably on the order of 5 wt.% at most.

The present invention further provides a module for detection of $NO_x$ gas in a mixed gas which comprises
  (i) an electric insulating support,
  (ii) the above element for detection of $NO_x$ gas of the invention integrated into the surface of the support, and
  (iii) a couple of electrodes connected to the element for detection of $NO_x$ gas at intervals of distance;
and a module for detection of $NO_x$ gas in a mixed gas which comprises the above module to which a means to maintain the temperature of the $NO_x$ gas-detecting element at about 200° to about 700° C., preferably at about 400° to about 600° C., is added as an constitutive element.

The present invention still further provides a device for measurement of $NO_x$ gas concentration in a mixed gas which comprises
  (i) an electric insulating support,
  (ii) the above element for detection of $NO_x$ gas of the invention integrated into the surface of the support,
  (iii) a couple of electrodes connected to the element for detection of $NO_x$ gas at intervals of distance;
  (iv) a heating means to maintain the element for detection of $NO_x$ gas at a temperature of about 200° to about 700° C., preferably about 400° to about 600° C., and
  (v) a means to measure the electric resistance of the element for detection of $NO_x$ gas which resistance depends on the $NO_x$ gas concentration in the mixed gas to be measured.

The present invention still further provides a process for measurement of $NO_x$ gas concentration in a mixed gas, particularly in an exhaust gas, in an internal combustion engine, which comprises
  (a) maintaining with heating the above element for detection of $NO_x$ gas of the invention at temperatures of about 200° to about 700° C., preferably about 400° to about 600° C.,
  (b) contacting the specimen mixed gas with the heated surface of the element for detection of $NO_x$ gas, and
  (c) measuring the electric resistance of the element for detection of $NO_x$ gas.

The above module for detection of $NO_x$ gas, device for measurement of $NO_x$ gas concentration and method for measurement of $NO_x$ gas concentration are described in more detail below in accordance with the attached FIGS. 1 and 2.

BRIEF DESCRIPTION OF THE DRAWINGS

The attached

FIG. 1 is a birds' eye-view showing a typical structure of the module for detection of $NO_x$ gas wherein the $NO_x$ gas-detecting element in a rectangular chip shape is used. That is, the module for detection of $NO_x$ gas has a structure wherein the $NO_x$ gas-detecting element 1 is placed in an electric insulating support 3 so that at least a part of the element is exposed, a couple of electrodes 2 are connected to the $NO_x$ gas-detecting element 1 at intervals of distance and a heater 4 is placed so as to be located near the $NO_x$ gas-detecting element 1 (electrodes for the heater are not indicated in the view). In the above module for detection of $NO_x$ gas the electric insulating support 3 is used for supporting $NO_x$ gas-detecting element 1, heater 4 and electrodes 2, and materials having an electric insulating property and heat resistance against the heating temperature by heater 4 are usable therefor without particular limitations. Alumina, $MgO$ $Al_2O_3$, AlN and the like are suitable as such materials. Heater 4 is used to heat the $NO_x$ gas-detecting element 1 to enhance the reactivity of the detecting element with $NO_x$. It is preferred that the above heater 4 is placed near $NO_x$ gas-detecting element 1 and placed so as to maintain with heating the $NO_x$ gas-detecting element 1 at a predetermined temperature through the electric insulating support 3. Specifically preferred is an embodiment wherein the heater 4 is buried in the electric insulating support 3 near the $NO_x$ gas-detecting element 1 as shown in FIG. 1, or an embodiment wherein the heater 4 is stuck on the surface other than the exposed surface of the $NO_x$ gas-detecting element 1.

Further, the material of heater 4 is not particularly limited so long as it can be heated to a predetermined temperature with electricity. Examples of suitable materials include platinum, tungsten, ruthenium oxide, silicon carbide, etc.

Figure 2:
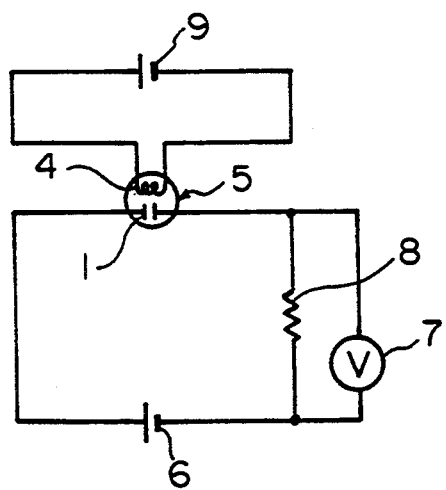
FIG. 2 shows a typical electric circuit diagram of the device for measurement of $NO_x$ gas concentration of the present invention.

FIG. 2 shows a typical circuit diagram of the device for measurement of the concentration of $NO_x$ gas into which the module for detection of $NO_x$ gas is integrated. That is, the module for detection of $NO_x$ gas 5 is serially connected to a power source for circuit 6 and volt meter 7 through electrodes. Further, load resistance 8 is connected in parallel to volt meter 7. Further, heater 4 in the module is connected to a power source 9 for the heater.

In measurement of $NO_x$ gas concentration using the above device for measurement of the concentration of $NO_x$ gas, heater 4 is made to operate, the $NO_x$ gas-detecting element 1 is placed in a mixed gas as a specimen while the $NO_x$ gas-detecting element 1 is heated to a predetermined temperature, for example, to about 200° to about 700° C., preferably about 400° to about 600° C., and the voltage at that time is measured by volt meter 7.

That is, there is the following relation among the voltage $V_c$ of power source 6 for circuit, the resistance $R_L$ of load resistance 8, output voltage $V_{out}$ measured by volt meter 7 and the resistance $R_s$ of the $NO_x$ gas-detecting element, and $R_s$ can easily be calculated according to the following equation (1) by measuring $V_{out}$:

$$R_s = R_L(V_c - V_{out})/V_{out} \quad (1)$$

The $NO_x$ gas-detecting element of the invention exhibits, when the temperature of the element is constant, a definite resistance in accordance with the concentration of NO or $NO_2$ in the atmosphere and moreover almost equal resistances in respect of NO and $NO_2$. Thus, it is possible to know the $NO_x$ gas concentration in the specimen mixed gas by determining $NO_x$ gas concentration from a previously prepared calibration curve using the thus obtained $R_s$ value.

EFFECT

The $NO_x$ gas-detecting element of the invention has functions, for example, that
(1) it has high and almost equal sensitivities to both NO and $NO_2$,
(2) it has an adequate sensitivity even to $NO_x$ gas in high concentration,
(3) it hardly undergo influences of other coexisting gases.

Therefore, it is possible to accurately measure $NO_x$ concentration in a mixed gas containing $NO_x$ over a wide range using the $NO_x$ gas-detecting element of the invention.

Above all, (b-1) and (c-1) of the $NO_x$ gas-detecting elements in this invention have excellent characteristics to detect $NO_x$ gas in a high concentration.

It is possible to detect $NO_x$ concentration in a general mixed gas by use of the $NO_x$ gas-detecting element of the invention. However, as the detecting element has characteristics that it has an adequately large sensitivity to $NO_x$ gas in higher concentration and does not undergo the influence of other coexisting gases, the detecting element is particularly suitable for continuously monitoring $NO_x$ concentration by directly setting the element inside the flue of internal combustion engines, etc. and changing the resistance of the element. Further, it is also possible to develop the element for a feedback system wherein resistance change of the element is obtained and the operation conditions for internal combustion engines, etc. are altered once an abnormal state takes place.

EXAMPLE

The present invention is specifically described below by examples, but not limited thereto.

The sensitivities of NO, $NO_2$, $O_2$ and CO and the value of the nonstoichiometric parameter ($\delta$) in the following Examples 1 to 40 were determined by the following methods, respectively:

(1) NO Sensitivity

Represented by the ratio log ($R_2/R_1$) of the resistance $R_2$ in an $N_2$ gas atmosphere containing 5% $O_2$ and 1,000 ppm NO to the resistance $R_1$ in an $N_2$ gas atmosphere containing 5% $O_2$ and 100 ppm NO.

(2) $NO_2$ Sensitivity

Represented by the ratio log ($R_2/R_1$) of the resistance $R_2$ in an $N_2$ gas atmosphere containing 5% $O_2$ and 1,000 ppm $NO_2$ to the resistance $R_1$ in an $N_2$ gas atmosphere containing 5% $O_2$ and 100 ppm $NO_2$.

(3) $O_2$ Sensitivity

Represented by the ratio log ($R_2/R_1$) of the resistance $R_2$ in an $N_2$ gas atmosphere containing 900 ppm NO, 100 ppm $NO_2$ and 10% $O_2$ to the resistance $R_1$ in an $N_2$ gas atmosphere containing 900 ppm NO, 100 ppm $NO_2$ and 1% $O_2$.

(4) CO Sensitivity

Represented by the ratio log ($R_2/R_1$) of the resistance $R_2$ in an $N_2$ gas atmosphere containing 5% $O_2$, 900 ppm NO, 100 ppm $NO_2$ and 1,000 ppm CO to the resistance $R_1$ in an $N_2$ gas atmosphere containing 5% $O_2$, 900 ppm NO, 100 ppm $NO_2$ and 10 ppm CO.

(5) The value of the nonstoichiometric parameter ($\delta$)

The value of the nonstoichiometric parameter ($\delta$) means a value calculated from the amount of each element measured using an ESCA (X-ray photoelectron spectral apparatus; using JPS-80 of JEOL.

It can be said that the larger the value represented by the above log ($R_2/R_1$) is, the higher the sensitivity to that gas is.

EXAMPLE 1

An aqueous ammonium sulfate solution and ammonia were added to an aqueous $TiCl_4$ solution, and the formed precipitate was filtered, washed and burned in the air at 900° C. for one hour. The obtained burned powder (having a $\delta$-value of 0.01) was placed in a cavity, Pt electrodes were buried in the both sides, and then the powder was compression-molded to obtain a chip-like molding having a shape shown in FIG. 1. This chip-like molding was burned in the air at 1,200° C. for 4 hours to obtain a sintered body of $TiO_{2-\delta}$. The value of $\delta$ in the obtained sintered body $TiO_{2-\delta}$ was 0.05. The above chip-like molding had a thickness of 1 mm and longitudinal and transverse lengths of 2 mm and 2 mm, respectively.

Figure 1:
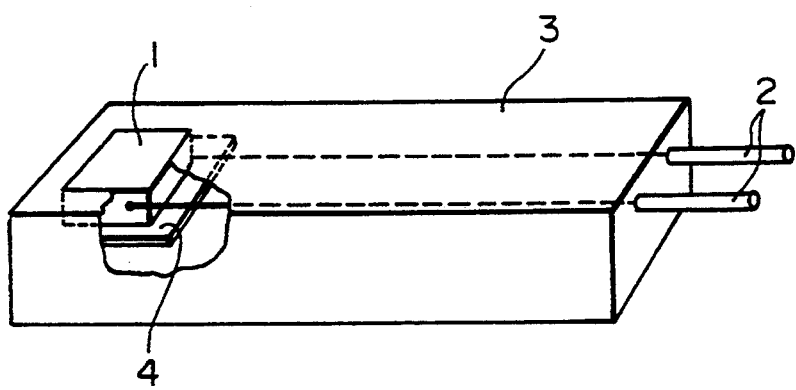
FIG. 1 is a bird's eye-view exhibiting embodiments of the $NO_x$ gas-detecting element and module for detection of $NO_x$ gas wherein the element is used.

An $NO_x$ gas-detecting module having the structure shown in FIG. 1 was assembled using the above $TiO_{2-\delta}$ chip. In this $NO_x$ gas-detecting module $Al_2O_3$ and platinum were used as the insulating substrate and the heater, respectively.

Sensitivity to various gases was measured using the thus obtained $NO_x$ gas-detecting device. The measurement was made under the condition that the $NO_x$ gas-detecting element was placed in the predetermined gases while being heated to 500° C.

The results were exhibited in Table 1.

COMPARATIVE EXAMPLE 1

$TiO_2$ powder was molded into a chip-like form in the same manner as in Example 1 and then burned in oxygen at 900° C. for 4 hours. The $\delta$ value of $TiO_{2-\delta}$ of the obtained sintered body was 0. Sensitivities of the obtained chip-like sintered body to various gases were measured in the same manner as in Example 1. As the result were obtained NO sensitivity of 0.08, $NO_2$ sensitivity of 0.09, $O_2$ sensitivity of 0.41 and CO sensitivity of 0.32.

EXAMPLES 2 to 16

Solid solutions shown in Examples 2 to 16 in the following Table 1 were prepared. Preparation of each solid solution was conducted by mixing an oxide of the element which is indicated in Table 1 and is to be contained in $TiO_2$ in the solid-solution state with $TiO_2$ in a predetermined molar ratio and then burning the mixture in the air at 1,000° C. for one hour. As a result of ascertainment by X-ray diffraction, all of the obtained solid solutions exhibited diffraction peak of rutile type $TiO_2$ alone. It was ascertained by this that in each of the titanium-containing oxides of Examples 2 to 16 the added element is contained in $TiO_2$ in the solid-solution state.

The obtained solid solution was molded into a chip-like form in the same manner as in Example 1 and then burned in the air at 1,200° C. for 4 hours to obtain a chip-like sintered body shown in FIG. 1. The nonstoichiometric parameters of the obtained chip-like sintered bodies are shown in Table 1. $NO_x$ sensitivity, $O_2$ sensitivity and CO sensitivity were measured about these chip-like sintered bodies in the same manner as in Example 1. The results are shown in Table 1.

It is understood from these results that the $NO_x$ gas-detecting elements of the invention have a high sensitivity to $NO_x$ in high concentrations and do not undergo influence of the other components in the gas.

EXAMPLES 17 to 28

Titanium-containing oxides having a perovskite structure shown in Examples 17 to 28 in the following Table 1 were prepared. Preparation of these titanium-containing oxides was carried out by mixing a carbonate of metal other than titanium indicated in Table 1 with $TiO_2$ in a predetermined molar ratio and burning the mixture in the air at 1,200° C. for one hour.

As a result of ascertainment by X-ray diffraction it was ascertained from the fact that each of the obtained titanium-containing oxides exhibited only peaks peculiar to an oxide of a perovskite structure that it is an oxide having a perovskite structure.

Each of the thus obtained oxide having a perovskite structure, and a mixture of each of the thus obtained oxides having a perovskite structure with the titanium oxide powder obtained in Example 1 in a molar ratio of 1:1 was molded into a chip-like form in the same manner as in Example 1 and then burned in the air at 1,200° C. for 4 hours to obtain a chip-like sintered body shown in FIG. 1. Nonstoichiometric parameters of the obtained chip-like sintered bodies are shown in Table 1. These chip-like sintered bodies were measured for $NO_x$ sensitivity, $O_2$ sensitivity and CO sensitivity in the same manner as in Example 1. The results are shown in Table 1.

It is seen from these results that the $NO_x$ gas-detecting elements of the invention have a high sensitivity to $NO_x$ in high concentration and moreover does not undergo influence of the coexisting matters.

COMPARATIVE EXAMPLE 2

$SnO_2$ powder was molded into a chip-like form in the same manner as in Example 1 and burned in the air at 1,200° C. for 4 hours to obtain a chip-like sintered body having a nonstoichiometric parameter ($\delta$) indicated in Table 1. The obtained chip-like sintered bodies were measured for sensitivity to various gases in the same manner as in Example 1. The results are shown in Table 1.

TABLE 1

| | $NO_x$ gas-detecting element | | Sensitivity to various gases | | | |
|---|---|---|---|---|---|---|
| | Kind of oxide | ($\delta$) | NO sensitivity | $NO_2$ sensitivity | $O_2$ sensitivity | CO sensitivity |
| Example | | | | | | |
| 1 | $TiO_2$ | 0.05 | 0.67 | 0.61 | 0.03 | 0.03 |
| 2 | $Al_{0.01}Ti_{0.99}O_2$ | 0.08 | 0.68 | 0.60 | 0.08 | 0.05 |
| 3 | $Al_{0.08}Ti_{0.92}O_2$ | 0.05 | 0.60 | 0.52 | 0.10 | 0.09 |
| 4 | $Nb_{0.05}Ti_{0.95}O_2$ | 0.20 | 0.49 | 0.58 | 0.09 | 0.08 |
| 5 | $Ta_{0.03}Ti_{0.97}O_2$ | 0.18 | 0.50 | 0.55 | 0.08 | 0.09 |
| 6 | $Sb_{0.02}Ti_{0.98}O_2$ | 0.15 | 0.55 | 0.60 | 0.09 | 0.09 |
| 7 | $As_{0.01}Ti_{0.99}O_2$ | 0.13 | 0.52 | 0.60 | 0.08 | 0.07 |
| 8 | $Ga_{0.003}Ti_{0.997}O_2$ | 0.09 | 0.65 | 0.60 | 0.05 | 0.06 |
| 9 | $In_{0.005}Ti_{0.995}O_2$ | 0.10 | 0.63 | 0.61 | 0.06 | 0.05 |
| 10 | $Sc_{0.01}Ti_{0.99}O_2$ | 0.11 | 0.68 | 0.63 | 0.05 | 0.04 |
| 11 | $Sc_{0.08}Ti_{0.92}O_2$ | 0.08 | 0.58 | 0.53 | 0.11 | 0.11 |
| 12 | $Mg_{0.05}Ti_{0.95}O_2$ | 0.15 | 0.62 | 0.59 | 0.06 | 0.05 |
| 13 | $Y_{0.01}Ti_{0.99}O_2$ | 0.13 | 0.65 | 0.60 | 0.06 | 0.06 |
| 14 | $Al_{0.01}Nb_{0.01}Ti_{0.98}O_2$ | 0.13 | 0.53 | 0.58 | 0.08 | 0.08 |
| 15 | $Sc_{0.01}Sb_{0.01}Ti_{0.98}O_2$ | 0.15 | 0.55 | 0.58 | 0.07 | 0.07 |
| 16 | $In_{0.01}Ta_{0.01}Ti_{0.98}O_2$ | 0.12 | 0.55 | 0.55 | 0.07 | 0.09 |
| 17 | $BaTiO_3$ | 0.10 | 0.71 | 0.63 | 0.02 | 0.01 |
| 18 | $PbTiO_3$ | 0.06 | 0.67 | 0.60 | 0.03 | 0.03 |
| 19 | $CdTiO_3$ | 0.05 | 0.66 | 0.59 | 0.03 | 0.04 |
| 20 | $CaTiO_3$ | 0.09 | 0.65 | 0.57 | 0.01 | 0.01 |
| 21 | $SrTiO_3$ | 0.08 | 0.71 | 0.63 | 0.02 | 0.01 |
| 22 | $LaTiO_3$ | 0.08 | 0.68 | 0.62 | 0.05 | 0.04 |
| 23 | $BaTiO_3 + TiO_2$ | 0.12 | 0.71 | 0.63 | 0.07 | 0.02 |
| 24 | $CaTiO_3 + TiO_2$ | 0.10 | 0.64 | 0.60 | 0.08 | 0.04 |
| 25 | $SrTiO_3 + TiO_2$ | 0.11 | 0.65 | 0.60 | 0.06 | 0.03 |

TABLE 1-continued

| | $NO_x$ gas-detecting element | | Sensitivity to various gases | | | |
|---|---|---|---|---|---|---|
| | Kind of oxide | ($\delta$) | NO sensitivity | $NO_2$ sensitivity | $O_2$ sensitivity | CO sensitivity |
| 26 | $Sr_{0.9}Ca_{0.1}TiO_3$ | 0.09 | 0.69 | 0.63 | 0.02 | 0.01 |
| 27 | $Ba_{0.9}La_{0.1}TiO_3$ | 0.13 | 0.68 | 0.62 | 0.04 | 0.02 |
| 28 | $Ca_{0.9}La_{0.1}TiO_3$ | 0.14 | 0.63 | 0.60 | 0.04 | 0.03 |
| Comparative Example 2 | $SnO_2$ | 0.02 | 0.08 | 0.19 | 0.20 | 0.35 |

EXAMPLES 29 to 34

Titanium-containing oxides containing Ga in various proportions indicated in the following Table 2 and in the solid-solution state were prepared. That is, $Ga_2O_3$ and $TiO_2$ were mixed in various proportions so that the atomic percentages of Ga to Ti became the values indicated in Table 2, and each mixture was burned in the air at 1,000° C. for one hour to prepare a composite oxide. As a result of measurement by X-ray diffraction it was ascertained that each of the obtained composite oxides exhibited only the diffraction peak of rutile type $TiO_2$ and thus the entire gallium is contained in $TiO_2$ in the solid-solution state.

Each of the composite oxides was molded into a chip-like form in the same manner as in Example 1 and then burned in the air at 1,300° C. for 10 hours to obtain a chip-like sintered body indicated in Table 2. Nonstoichiometric parameters of the obtained chip-like sintered bodies are indicated in Table 2. These chip-like sintered bodies were measured for $NO_x$ sensitivity, $O_2$ sensitivity and CO sensitivity in the same manner as in Example 1. The results are shown in Table 2.

TABLE 2

| | $NO_x$ gas-detecting element | | Sensitivity to various gases | | | |
|---|---|---|---|---|---|---|
| Example | Atomic percentage of Ga | ($\delta$) | NO sensitivity | $NO_2$ sensitivity | $O_2$ sensitivity | CO sensitivity |
| Example | | | | | | |
| 29 | 0.01 | 0.10 | 0.48 | 0.49 | 0.10 | 0.07 |
| 30 | 0.05 | 0.13 | 0.69 | 0.63 | 0.08 | 0.05 |
| 31 | 0.1 | 0.13 | 0.65 | 0.61 | 0.07 | 0.04 |
| 32 | 0.5 | 0.15 | 0.59 | 0.58 | 0.08 | 0.04 |
| 33 | 1 | 0.15 | 0.52 | 0.50 | 0.07 | 0.05 |
| 34 | 5 | 0.14 | 0.45 | 0.45 | 0.10 | 0.09 |

EXAMPLES 35 to 39

The procedure of Example 31 was repeated except that as the burning conditions of the chip-like molding was employed the conditions that the chip-like molding was burned at 1,000° C. for 10 hours in $N_2$ containing $H_2$ in various concentrations indicated in the following Table 3, whereby chip-like sintered bodies were obtained.

The nonstoichiometric parameters ($\delta$) of the resulting chip-like sintered bodies are indicated in Table 3. These chip-like sintered bodies were measured for $NO_x$ sensitivity, $O_2$ sensitivity and CO sensitivity in the same manner as in Example 1. The results are shown in Table 3.

COMPARATIVE EXAMPLES 3 and 4

The procedure of Examples 35 to 39 was repeated except that different $H_2$ concentrations in the burning atmosphere were adopted to obtain chip-like sintered bodies. $H_2$ concentrations, nonstoichiometric parameters ($\delta$) and the measured $NO_x$ sensitivities, $O_2$ sensitivities and CO sensitivities are shown in Table 3.

It is seen from these results that the $NO_x$ gas-detecting elements of the invention have a high sensitivity to $NO_x$ in high concentration and moreover do not undergo influence of the coexisting matters.

TABLE 3

| | $NO_x$ gas-detecting element | | Sensitivity to various gases | | | |
|---|---|---|---|---|---|---|
| Example | $H_2$ concentration (%) | ($\delta$) | NO sensitivity | $NO_2$ sensitivity | $O_2$ sensitivity | CO sensitivity |
| Example | | | | | | |
| 35 | 0.05 | 0.04 | 0.48 | 0.50 | 0.10 | 0.05 |
| 36 | 0.1 | 0.07 | 0.60 | 0.55 | 0.08 | 0.04 |
| 37 | 0.5 | 0.10 | 0.68 | 0.63 | 0.08 | 0.02 |
| 38 | 1 | 0.14 | 0.63 | 0.58 | 0.07 | 0.03 |
| 39 | 4 | 0.18 | 0.48 | 0.45 | 0.08 | 0.03 |
| Comparative Example | | | | | | |
| 3 | 0.01 | 0.005 | 0.10 | 0.23 | 0.20 | 0.25 |
| 4 | 20 | 0.61 | 0.12 | 0.08 | 0.08 | 0.04 |

EXAMPLE 40

An exhaust gas from automobile was analyzed for $NO_x$ concentration using the $NO_x$ gas-detecting devices of Examples 1 to 39 and Comparative Example 2 and a chemiluminescence type $NO_x$-detecting device. The adopted operation conditions of the engine was such that the engine speed was 1,500 ppm and A/F was in the range of 13 to 20. As a result of comparison of the analytical value by each detecting device it was found that the analytical value by the chemiluminescence type $NO_x$-detecting device and the analytical values by the detecting-devices using the titanium-containing oxides of Examples 1 to 39 respectively well accorded with one another and thus by the detecting devices of the invention $NO_x$ gas can accurately be detected up to high concentration without undergoing influences due to change of the concentration of the coexisting gas such as $O_2$, CO or HC in the exhaust gas. On the other hand, the analytical value by the detecting device of Comparative Example 2 using $SnO_2$ was largely different from the analytical value on $NO_x$ concentration by the chemiluminescence type $NO_x$-detecting device.

In the following Examples 41 to 81, NO, CO and HC sensitivities were determined according to the following methods, respectively.

(1) NO Sensitivity

Represented by the ratio log ($R_2/R_1$) of the resistance $R_2$ in an $N_2$ gas atmosphere containing 5% $O_2$ and 1,000 ppm NO to the resistance $R_1$ in an $N_2$ gas atmosphere containing 5% $O_2$. No NO was listed as present in the atmosphere for measure $R_1$.

(2) CO Sensitivity

Represented by the ratio log ($R_2/R_1$) of the resistance $R_2$ in an $N_2$ gas atmosphere containing 5% $O_2$, 500 ppm NO and 5,000 ppm CO to the resistance $R_1$ in an $N_2$ gas atmosphere containing 5% $O_2$, 500 ppm NO and 50 ppm CO.

(3) $H_2$ Sensitivity

Represented by the ratio log ($R_2/R_1$) of the resistance $R_2$ in an $N_2$ gas atmosphere containing 5% $O_2$, 500 ppm NO and 5,000 ppm $H_2$ to the resistance $R_1$ in an $N_2$ gas atmosphere containing 5% $O_2$, 500 ppm NO and 50 ppm $H_2$.

(4) HC Sensitivity

Represented by the ratio log ($R_2/R_1$) of the resistance $R_2$ in an $N_2$ gas atmosphere containing 5% $O_2$, 500 ppm NO and 5,000 ppm $C_3H_6$ to the resistance $R_1$ in an $N_2$ gas atmosphere containing 5% $O_2$, 500 ppm NO and 50 ppm $C_3H_6$.

(5) $O_2$ Sensitivity $R_1$; NO900 ppm+$NO_2$100 ppm+$N_2$+$O_2$ 0.1%

$R_2$; NO900 ppm+$NO_2$100 ppm+$N_2$+$O_2$ 10%

It can be said that the larger the value represented by the above log ($R_2/R_1$) is, the higher the the sensitivity to the gas is.

EXAMPLE 41

An aqueous ammonium sulfate solution and ammonia were added to an aqueous $TiCl_4$ solution, and the formed precipitate was filtered, washed and burned in the air at 900° C. for one hour. The resulting burned powder was placed in a cavity, and after burial of Pt electrodes into both ends compression molded into a chip-like molding shown in FIG. 1. This chip-like molding was burned in the air at 1,200° C. for 4 hours to obtain a sintered body of $TiO_{2-\delta}$. The value of $\delta$ in the $TiO_{2-\delta}$ sintered body was 0.05. The size of the chip-like molding was such that the thickness was 1 mm and the longitudinal and transverse lengths were 2 mm and 2 mm, respectively.

An $NO_x$ gas-detecting module having the structure shown in FIG. 1 was produced using the above chip of $TiO_{2-\delta}$. In this $NO_x$ gas-detecting module $Al_2O_3$ and platinum were used as the insulating substrate and heater, respectively.

Sensitivity to various gases was measured using the thus obtained $NO_x$ gas-detecting device. The measurement was carried out by placing the $NO_x$ gas-detecting element in the predetermined gases while heating it to 500° C. by means of the heater.

The results are shown in Table 4.

EXAMPLES 42 to 44

An aqueous ammonium sulfate solution and ammonia were added to an aqueous $TiCl_4$ solution, and the formed precipitate was filtered, washed and burned in the air at 900° C. for one hour. Then, aqueous $H_2PtCl_6$, $H_2PdCl_4$ and $RhCl_3 \cdot 4H_2O$ solution were added to $TiO_2$ respectively so that Pt, Pd and Rh contents became 300 ppm respectively, and after drying the mixtures were burned at 500° C. for one hour. The resulting powders were molded into a chip-like form in the same manner as in Example 41 and burned in the air at 1,200° C. for 4 hours, respectively. These chip-like sintered bodies were measured for sensitivity to the various gases in the same manner as in Example 41.

The results are shown in Table 4.

EXAMPLES 45 to 47

The $Pt/TiO_2$ powder (Pt=300 or 800 ppm) or $Pd/TiO_2$ powder (Pd=800 ppm) obtained in the same manner as in Examples 42 to 44 respectively was applied onto the surface of the chip of $TiO_{2-\delta}$ obtained in Example 41 and burned in the air at 1,200° C. for one hour. This chip-like sintered body was measured for sensitivity to the various gases in the same manner as in Example 41.

The results are shown in Table 4.

EXAMPLE 48

NiO was compounded into $TiO_2$ so that the content became one wt.%, and the mixture was burned in the air at 1,200° C. for one hour. The resulting powder was applied onto the surface of the chip of $TiO_{2-\delta}$ obtained in Example 41 and burned in the air at 1,200° C. for one hour. This chip-like sintered body was measured for the various gases in the same manner as in Example 41.

The results are shown in Table 4.

EXAMPLE 49

$LaCO_3$ and $Co(CH_3COO)_2$ were mixed so that the molar ratio was 1:1, and burned in the air at 1,200° C. for one hour. The resulting powder was applied onto the surface of the chip of $TiO_{2-\delta}$ obtained in Example 41 and burned in the air at 1,000° C. for one hour. This chip-like sintered body was measured for sensitivity to the various gases in the same manner as in Example 41.

The results are shown in Table 4.

EXAMPLES 50 to 62

Solid solutions indicated in Examples 50 to 62 in the following Table 4 were prepared. Each solid solution was prepared by mixing the oxide of element indicated in Table 4 with $TiO_2$ in a predetermined molar ratio and burning the mixture in the air at 1,000° C. for one hour.

As a result of ascertainment by X-ray diffraction each of the resulting solid solutions exhibited only diffraction peaks of rutile type $TiO_2$. It was ascertained from this fact that in all of the titanium-containing oxides of Examples 50 to 62 the added element was contained in $TiO_2$ in the solid-solution state. The thus obtained solid solutions were molded respectively into a chip-like form in the same manner as in Example 41 and burned in the air at 1,200° C. for 4 hours to obtain chip-like sintered bodies indicated in Examples 50 to 62 in the following Table 4. The Pt/TiO$_2$ powder obtained in Example 42 was applied onto the surface of each of the obtained chip-like sintered bodies and burned in the air at 1,200° C. for one hour. The resulting chip-like sintered bodies were measured for sensitivity to the various gases in the same manner as in Example 41. The results are shown in Table 4.

EXAMPLES 63 to 74

Titanium-containing oxides having a perovskite structure indicated in Examples 63 to 74 in the following Table 4 were prepared. Preparation of these titanium-containing oxides was carried out by mixing the carbonate of metals other than titanium indicated in Table 4 with TiO$_2$ in a predetermined molar ratio and burning the mixture in the air at 1,200° C. for one hour. As a result of ascertainment by X-ray diffraction all of the resulting titanium-containing oxides exhibited only peaks peculiar to oxides of a perovskite structure, whereby it was ascertained that they are oxides of a perovskite structure.

Each of the thus obtained oxide having a perovskite structure, and a mixture of one of the thus obtained oxides of a perovskite structure with the titanium oxide powder obtained in Example 41 in a molar ratio of 1:1 was molded into a chip-like form in the same manner as in Example 41, and burned in the air at 1,200° C. for 4 hours to obtain a chip-like sintered body indicated in Examples 63 to 74 in the following Table 4. The Pt/TiO$_2$ powder obtained in Example 42 was applied onto the surface of each chip-like sintered body and burned in the air at 1,200° C. for one hour. The resulting chip-like sintered bodies were measured for sensitivity to the various gases in the same manner as in Example 41. The results are shown in Table 4.

EXAMPLES 75 to 81

Titanium-containing oxides were prepared which contain Ga in the various rates indicated in Examples 75 to 81 in the following Table 4 in the solid-solution state. That is, Ga$_2$O$_3$ and TiO$_2$ were mixed in the predetermined rates and burned in the air at 1,000° C. for 1 hour to obtain titanium-containing oxides. It was found as a result of ascertainment by X-ray diffraction that the oxides exhibited only the diffraction peaks of rutile type TiO$_2$ and all the Ga was contained in TiO$_2$ in the solid-solution state. The oxides were respectively molded into a chip-like form in the same manner as in Example 41 and burned in the air at 1,300° C. for 10 hours to obtain chip-like sintered bodies. On the other hand, H$_2$PtCl$_2$ was added to Al$_2$O$_3$ so that the content became 300 ppm, and after drying the mixture was burned at 500° C. for one hour to give oxidation catalyst powder. This powder was applied onto the surface of each of the chip-like sintered bodies and burned in the air at 1,200° C. for one hour. The resulting chip-like sintered bodies were measured for sensitivity to the various gases in the same manner as in Example 41.

The results are shown in Table 4.

COMPARATIVE EXAMPLES 5 and 6

Chip-like sintered bodies were obtained as in Examples 75 to 81 except that titanium oxide having a δ value of 0.01 or 0 was used and the surface contained 0.5% of Pt or 5% of Pt. The resulting chip-like sintered bodies were measured for sensitivity to various gases in the same manner as in Example 41.

The results are shown in Table 4.

TABLE 4

| | NO$_x$ gas-detecting element | | | Sensitivity to various gases | | | | |
|---|---|---|---|---|---|---|---|---|
| | Kind of oxide | (δ) | Oxidation catalyst | NO sensitivity | CO sensitivity | H$_2$ sensitivity | HC sensitivity | O$_2$ sensitivity |
| Example | | | | | | | | |
| 41 | TiO$_2$ | 0.05 | — | 1.20 | 0.08 | 0.06 | 0.15 | 0.15 |
| 42 | " | 0.03 | Pt 300 ppm | 1.16 | 0.02 | 0.02 | 0.05 | 0.12 |
| 43 | " | 0.04 | Pd 300 ppm | 1.17 | 0.03 | 0.02 | 0.05 | 0.10 |
| 44 | " | 0.03 | Rh 300 ppm | 1.17 | 0.01 | 0.01 | 0.04 | 0.09 |
| 45 | " | 0.05 | Pt 300 ppm (/TiO$_2$) | 1.16 | 0.03 | 0.03 | 0.06 | 0.14 |
| 46 | " | 0.05 | Pt 800 ppm (/TiO$_2$) | 1.05 | 0.02 | 0.06 | 0.05 | 0.12 |
| 47 | " | 0.05 | Pd 800 ppm (/TiO$_2$) | 1.03 | 0.01 | 0.08 | 0.06 | 0.10 |
| 48 | " | 0.05 | Ni 1% | 1.18 | 0.07 | 0.06 | 0.08 | 0.15 |
| 49 | " | 0.05 | LaCoO$_3$ 1% | 1.08 | 0.05 | 0.05 | 0.08 | 0.15 |
| 50 | Al$_{0.01}$Ti$_{0.99}$O$_2$ | 0.07 | Pt 300 ppm (/TiO$_2$) | 1.25 | 0.01 | 0.09 | 0.02 | 0.10 |
| 51 | Nb$_{0.05}$Ti$_{0.95}$O$_2$ | 0.16 | Pt 300 ppm (/TiO$_2$) | 1.08 | 0.04 | 0.06 | 0.08 | 0.19 |
| 52 | Ta$_{0.03}$Ti$_{0.97}$O$_2$ | 0.15 | " | 1.08 | 0.03 | 0.06 | 0.07 | 0.18 |
| 53 | Sb$_{0.02}$Ti$_{0.98}$O$_2$ | 0.12 | " | 1.10 | 0.03 | 0.04 | 0.05 | 0.20 |
| 54 | As$_{0.01}$Ti$_{0.99}$O$_2$ | 0.10 | " | 1.15 | 0.02 | 0.04 | 0.05 | 0.19 |
| 55 | Ga$_{0.003}$Ti$_{0.997}$O$_2$ | 0.09 | " | 1.30 | 0.01 | 0.02 | 0.03 | 0.11 |
| 56 | Ta$_{0.005}$Ti$_{0.995}$O$_2$ | 0.09 | " | 1.29 | 0.01 | 0.03 | 0.02 | 0.15 |
| 57 | Sc$_{0.01}$Ti$_{0.99}$O$_2$ | 0.10 | " | 1.25 | 0.02 | 0.04 | 0.03 | 0.12 |
| 58 | Mg$_{0.05}$Ti$_{0.95}$O$_2$ | 0.13 | " | 1.25 | 0.03 | 0.02 | 0.03 | 0.10 |
| 59 | Y$_{0.01}$Ti$_{0.99}$O$_2$ | 0.12 | " | 1.28 | 0.02 | 0.02 | 0.02 | 0.13 |
| 60 | Al$_{0.01}$Nb$_{0.01}$Ti$_{0.98}$O$_2$ | 0.10 | " | 1.08 | 0.03 | 0.04 | 0.06 | 0.18 |
| 61 | Sc$_{0.01}$Sb$_{0.01}$Ti$_{0.98}$O$_2$ | 0.13 | Pt 300 ppm (/TiO$_2$) | 1.10 | 0.04 | 0.05 | 0.06 | 0.19 |
| 62 | In$_{0.01}$Ta$_{0.01}$Ti$_{0.98}$O$_2$ | 0.11 | " | 1.12 | 0.04 | 0.04 | 0.05 | 0.17 |
| 63 | BaTiO$_3$ | 0.09 | " | 1.29 | 0.03 | 0.03 | 0.06 | 0.20 |
| 64 | PbTiO$_3$ | 0.06 | " | 1.14 | 0.02 | 0.02 | 0.05 | 0.18 |
| 65 | CdTiO$_3$ | 0.05 | " | 1.20 | 0.01 | 0.02 | 0.03 | 0.13 |
| 66 | CaTiO$_3$ | 0.09 | " | 1.10 | 0.02 | 0.02 | 0.03 | 0.03 |
| 67 | SrTiO$_3$ | 0.07 | " | 1.28 | 0.01 | 0.03 | 0.05 | 0.05 |
| 68 | LaTiO$_3$ | 0.06 | " | 1.18 | 0.03 | 0.04 | 0.07 | 0.15 |
| 69 | BaTiO$_3$ + TiO$_2$ | 0.12 | " | 1.20 | 0.01 | 0.02 | 0.05 | 0.12 |
| 70 | CaTiO$_3$ + TiO$_2$ | 0.09 | " | 1.18 | 0.02 | 0.03 | 0.04 | 0.04 |
| 71 | SrTiO$_3$ + TiO$_2$ | 0.09 | Pt 300 ppm (/TO$_2$) | 1.17 | 0.01 | 0.03 | 0.03 | 0.05 |
| 72 | Sr$_{0.9}$Ca$_{0.1}$TiO$_3$ | 0.09 | " | 1.20 | 0.01 | 0.04 | 0.06 | 0.04 |
| 73 | Ba$_{0.9}$La$_{0.1}$TiO$_3$ | 0.10 | " | 1.25 | 0.02 | 0.04 | 0.06 | 0.18 |

TABLE 4-continued

| | NO$_x$ gas-detecting element | | | Sensitivity to various gases | | | | |
| | Kind of oxide | (δ) | Oxidation catalyst | NO sensitivity | CO sensitivity | H$_2$ sensitivity | HC sensitivity | O$_2$ sensitivity |
|---|---|---|---|---|---|---|---|---|
| 74 | Ca$_{0.9}$La$_{0.1}$TiO$_3$ | 0.12 | " | 1.22 | 0.01 | 0.03 | 0.05 | 0.08 |
| 75 | Ga$_{0.0001}$Ti$_{0.9999}$O$_2$ | 0.09 | Pt 300 ppm (/Al$_2$O$_3$) | 1.06 | 0.05 | 0.04 | 0.07 | 0.13 |
| 76 | Ga$_{0.0005}$Ti$_{0.9995}$O$_2$ | 0.12 | " | 1.30 | 0.02 | 0.02 | 0.04 | 0.10 |
| 77 | Ga$_{0.001}$Ti$_{0.999}$O$_2$ | 0.13 | " | 1.28 | 0.01 | 0.02 | 0.03 | 0.09 |
| 78 | Ga$_{0.005}$Ti$_{0.995}$O$_2$ | 0.13 | " | 1.25 | 0.01 | 0.02 | 0.05 | 0.09 |
| 79 | Ga$_{0.01}$Ti$_{0.99}$O$_2$ | 0.15 | " | 1.16 | 0.02 | 0.04 | 0.06 | 0.12 |
| 80 | Ga$_{0.05}$Ti$_{0.95}$O$_2$ | 0.14 | " | 1.06 | 0.05 | 0.06 | 0.06 | 0.13 |
| 81 | Ga$_{0.05}$Ti$_{0.95}$O$_2$ | 0.14 | — | 1.08 | 0.13 | 0.16 | 0.22 | 0.18 |
| Comparative Example | | | | | | | | |
| 5 | TiO$_2$ | 0.01 | Pt 0.5% | 0.32 | 0.19 | 0.58 | 0.39 | 0.45 |
| 6 | TiO$_2$ | 0 | Pt 5% | 0.08 | 0.02 | 0.01 | 0.03 | 0.50 |

What we claim is:

1. A module for detection of NO$_x$ gas in a mixed gas which comprises:
   (i) an electric insulating support,
   (ii) an element for detection of NO$_x$ gas integrated into the surface of the support, said element for detection of NO$_x$ gas substantially consisting of at least one titanium-containing oxide which is selected from the group consisting of:
   (a) titanium oxide,
   (b) a solid solution wherein at least one element selected from the group consisting of aluminum (Al), gallium (Ga), indium (In), scandium (Sc), magnesium (Mg), yttrium (Y), neodymium (Nd), tantalum (Ta), antimony (Sb) and arsenic (As) is contained in the solid-solution state in the titanium oxide, and
   (c) an oxide which contains titanium and as another element, lead (Pb) or cadmium (Cd), and has a perovskite structure,
   and has an oxygen deficiency such that its nonstoichiometric parameter (δ) is in the range of 0.03 to 0.3, and
   (iii) a couple of electrodes connected to the element for detection of NO$_x$ gas at intervals of distance.

2. The module of claim 1 which further comprises
   (iv) a heating means to maintain the element for detection of NO$_x$ gas at a temperature of about 200° to about 700° C.

3. The module of claim 1 wherein the titanium oxide of (a) in the element for detection of NO$_x$ gas is represented by the general formula:

TiO$_{2-δ}$ wherein δ is a nonstoichiometric parameter indicating a positive number in the range of 0.03 to 0.3.

4. The module of claim 1 wherein the solid solution of (b) in the element for detection of NO$_x$ gas is represented by the general formula:

A$_z$Ti$_{1-z}$O$_{2-δ}$ wherein δ is a nonstoichiometric parameter indicating a positive number in the range of 0.03 to 0.3; A represents at least one element selected from the group consisting of Al, Ga, In, Sc, Mg, Y, Nd, Ta, Sb and As; and z represents a positive number satisfying 0<z<0.1 when the element A is Al, Ga, In, Sc, Mg or Y and in the range satisfying 0<z<0.05 when the element A is Nd, Ta, Sb or As.

5. The module of claim 1 wherein the oxide of (c) in the element for detection of NO$_x$ gas is represented by the general formula:

BTiO$_{3-δ}$ wherein δ is a nonstoichiometric parameter indicating a positive number in the range of 0.03 to 0.3; and B represents Pb or Cd.

6. A device for measurement of NO$_x$ gas concentration in a mixed gas which comprises:
   (i) an electric insulating support,
   (ii) an element for detection of NO$_x$ gas integrated into the surface of the support, said element for detection of NO$_x$ gas substantially consisting of at least one titanium-containing oxide which is selected from the group consisting of:
   (a) titanium oxide,
   (b) a solid solution wherein at least one element selected from the group consisting of aluminum (Al), gallium (Ga), indium (In), scandium (Sc), magnesium (Mg), yttrium (Y), neodymium (Nd), tantalum (Ta), antimony (Sb) and arsenic (As) is contained in the solid-solution state in the titanium oxide, and
   (c) an oxide which contains titanium and as another element, lead (Pb) or cadmium (Cd), and has a perovskite structure,
   and has such an oxygen deficiency such that its nonstoichiometric parameter (δ) is in the range of 0.03 to 0.3,
   (iii) a couple of electrodes connected to the element for detection of NO$_x$ gas at intervals of distance,
   (iv) a heating means to maintain the element for detection of NO$_x$ gas at a temperature of about 200° to about 700° C., and
   (v) a means to measure the electric resistance of the element for detection of NO$_x$ gas which resistance depends on the NO$_x$ gas concentration in the mixed gas to be measured.

7. The device of claim 6 wherein the titanium oxide of (a) in the element for detection of NO$_x$ gas is represented by the general formula:

TiO$_{2-δ}$ wherein δ is a nonstoichiometric parameter indicating a positive number in the range of 0.03 to 0.3.

8. The device of claim 6 wherein the solid solution of (b) in the element for detection of NO$_x$ gas is represented by the general formula:

$$A_zTi_{1-z}O_{2-\delta}$$

wherein δ is a nonstoichiometric parameter indicating a positive number in the range of 0.03. to 0.3; A represents at least one element selected from the group consisting of Al, Ga, In, Sc, Mg, Y, Nd, Ta, Sb and As; and z represents a positive number satisfying $0<z<0.1$ when the element A is Al, Ga, In, Sc, Mg or Y and in the range satisfying $0<z<0.05$ when the element A is Nd, Ta, Sb or As.

9. The device of claim 6 wherein the oxide of (c) in the element for detection of $NO_x$ gas is represented by the general formula:

$$BTiO_{3-\delta}$$

wherein δ is a nonstoichiometric parameter indicating a positive number in the range of 0.03 to 0.3; and B represents Pb or Cd.

* * * * *